United States Patent
Klug et al.

(10) Patent No.: US 9,596,849 B2
(45) Date of Patent: *Mar. 21, 2017

(54) COMPOSITION CONTAINING SORBITAN MONOCAPRYLATE AND ALCOHOL

(75) Inventors: Peter Klug, Grossostheim (DE); Sonja Gehm, Bad Soden am Taunus (DE); Guiseppina Kluth, Kelkheim (DE); Franz-Xaver Scherl, Burgkirchen (DE); Maurice Frederic Pilz, Frankfurt am Main (DE)

(73) Assignee: Clariant International Ltd., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/321,199

(22) PCT Filed: May 11, 2010

(86) PCT No.: PCT/EP2010/002918
§ 371 (c)(1),
(2), (4) Date: Jan. 3, 2012

(87) PCT Pub. No.: WO2010/136120
PCT Pub. Date: Dec. 2, 2010

(65) Prior Publication Data
US 2012/0100085 A1    Apr. 26, 2012

(30) Foreign Application Priority Data

May 23, 2009 (DE) ................. 10 2009 022 445

(51) Int. Cl.
| | |
|---|---|
| A61K 8/92 | (2006.01) |
| A01P 1/00 | (2006.01) |
| A61Q 5/02 | (2006.01) |
| A61Q 17/04 | (2006.01) |
| A61Q 19/10 | (2006.01) |
| A01N 43/08 | (2006.01) |
| A61Q 15/00 | (2006.01) |
| A01N 31/14 | (2006.01) |
| A01N 31/04 | (2006.01) |
| A01N 43/16 | (2006.01) |
| A61K 8/34 | (2006.01) |
| A61K 8/49 | (2006.01) |
| A61Q 19/00 | (2006.01) |
| A61Q 1/04 | (2006.01) |
| A61Q 1/14 | (2006.01) |
| A61Q 5/06 | (2006.01) |
| A61Q 5/12 | (2006.01) |
| A61Q 19/08 | (2006.01) |

(52) U.S. Cl.
CPC ............ *A01N 31/14* (2013.01); *A01N 31/04* (2013.01); *A01N 43/08* (2013.01); *A01N 43/16* (2013.01); *A61K 8/34* (2013.01); *A61K 8/345* (2013.01); *A61K 8/4973* (2013.01); *A61Q 19/00* (2013.01); *A61K 2800/524* (2013.01); *A61Q 1/04* (2013.01); *A61Q 1/14* (2013.01); *A61Q 5/02* (2013.01); *A61Q 5/06* (2013.01); *A61Q 5/12* (2013.01); *A61Q 15/00* (2013.01); *A61Q 17/04* (2013.01); *A61Q 19/08* (2013.01); *A61Q 19/10* (2013.01)

(58) Field of Classification Search
CPC ....................................................... A01N 31/02
See application file for complete search history.

(56) References Cited

U.S. PATENT DOCUMENTS

| | | | |
|---|---|---|---|
| 3,331,742 A | | 7/1967 | Babayan |
| 4,637,930 A | * | 1/1987 | Konno et al. ................. 424/449 |
| 4,711,775 A | | 12/1987 | Dittmar et al. |
| 4,847,088 A | | 7/1989 | Blank |
| 6,413,529 B1 | | 7/2002 | Beerse et al. |
| 2003/0203070 A1 | * | 10/2003 | Lin et al. ........................ 426/25 |
| 2005/0222276 A1 | | 10/2005 | Schmaus et al. |
| 2007/0178144 A1 | | 8/2007 | Hameyer et al. |
| 2008/0142023 A1 | | 6/2008 | Schmid |

(Continued)

FOREIGN PATENT DOCUMENTS

| | | |
|---|---|---|
| CA | 1231046 | 1/1988 |
| DE | 3328372 | 3/1984 |

(Continued)

OTHER PUBLICATIONS

International Search Report for PCT/EP2010/002919 mail date Nov. 15, 2011.

(Continued)

*Primary Examiner* — Adam C Milligan
*Assistant Examiner* — Sarah Alawadi
(74) *Attorney, Agent, or Firm* — Tod A. Waldrop

(57) ABSTRACT

The invention relates to liquid compositions which contain a) from 5 to 95% by weight of sorbitan monocaprylate and b) from 5 to 95% by weight of one or more alcohols of formula (1)

$$R\text{—}OH \qquad (1),$$

wherein R is a group consisting of carbon, hydrogen and optionally oxygen atoms with 5 to 12, preferably 6 to 11, carbon atoms, and the carbon atoms can be interlinked in a linear, branched and/or cyclic fashion via saturated, unsaturated and/or aromatic carbon-carbon bonds and the groups can also contain ether units and hydrogen atoms and/or hydroxyl groups can be bound to the individual carbon atoms. The liquid compositions are suitable for the production of cosmetic, dermatological or pharmaceutical products.

8 Claims, No Drawings

(56) References Cited

U.S. PATENT DOCUMENTS

| | | | |
|---|---|---|---|
| 2008/0312195 A1* | 12/2008 | Simsch et al. ............... | 514/159 |
| 2010/0113664 A1 | 5/2010 | Bradshaw et al. | |
| 2011/0104085 A1 | 5/2011 | Klug et al. | |
| 2011/0117036 A1 | 5/2011 | Chaudhuri et al. | |
| 2012/0015893 A1 | 1/2012 | Herrwerth et al. | |
| 2012/0101135 A1 | 4/2012 | Klug et al. | |
| 2012/0116101 A1 | 5/2012 | Fuertes et al. | |
| 2014/0308224 A1 | 10/2014 | Pilz et al. | |
| 2014/0315996 A1 | 10/2014 | Pilz et al. | |
| 2014/0322151 A1 | 10/2014 | Fricke et al. | |
| 2014/0323564 A1 | 10/2014 | Pilz et al. | |
| 2014/0323592 A1 | 10/2014 | Pilz et al. | |
| 2014/0329870 A1 | 11/2014 | Pilz et al. | |
| 2014/0343171 A1 | 11/2014 | Pilz et al. | |
| 2014/0348763 A1 | 11/2014 | Pilz et al. | |
| 2014/0369943 A1 | 12/2014 | Pilz et al. | |
| 2015/0030553 A1 | 1/2015 | Pilz et al. | |
| 2016/0000080 A1 | 1/2016 | Pilz et al. | |

FOREIGN PATENT DOCUMENTS

| | | |
|---|---|---|
| DE | 2234009 | 12/1987 |
| EP | 1813251 | 8/2007 |
| EP | 1972330 | 9/2008 |
| EP | 2239315 | 10/2010 |
| JP | 59-175408 | 10/1984 |
| JP | H 01313408 | 12/1989 |
| JP | H 03168075 | 7/1991 |
| JP | 8173787 | 7/1996 |
| JP | 8187070 | 7/1996 |
| JP | H 09291016 | 11/1997 |
| JP | 2002541181 | 12/2002 |
| JP | 2003238396 | 8/2003 |
| JP | 2007203288 | 8/2007 |
| JP | 2008094755 | 4/2008 |
| JP | 2009078984 | 4/2009 |
| WO | WO 2006103338 | 10/2006 |
| WO | WO 2008119841 | 10/2008 |
| WO | WO 2008155159 | 12/2008 |
| WO | WO 2010108738 | 9/2010 |

OTHER PUBLICATIONS

International Preliminary Report on Patentability for PCT/EP2010/002919, dated Feb. 28, 2012.
Bach M. et al. Konservierungsmittel Und Ihre Praktische Anwendung in Kosmetischen Produkten, Sofw-Journal Seifen, Oele, Fette, Wachse, Verlag Fur Chemische Industrie, Angsburg, DE, vol. 116, No. 9, Jun. 13, 1990. pp. 942-7694, XP000134744.
International Search Report for PCT/EP2010/002918 mail date Jun. 30, 2011.
International Preliminary Report on Patentability for PCT/EP2010/002918.
Database CA (Online), Chemical Abstracts Service, Columbus, Ohio (Sep. 29, 2000), Fukushima Noriko; "Water-soluble rinses for dishwashers", XP002643077.
Database CA (Online), Chemical Abstracts Service, Columbus, Ohio (Aug. 14, 2008), Mori Toshiki; "Transparent cleaners comprising nonionic surfactants", XP002643078.
Database CA (Online), Chemical Abstracts Service, Columbus, Ohio (May 12, 1984), Miura Takeshi, Ishida Katsuo; "Rinsing assistants", XP002643079. English abstract of JP 51056809.
Database CA (Online), Chemical Abstracts Service, Columbus, Ohio (May 12, 1984), Miura Takeshi, Ishida Katsuo; "Rinsing assistants", XP002643080. English abstract of JP 51068608.
Database CA (Online), Chemical Abstracts Service, Columbus, Ohio (Sep. 18, 2003), Miura Takeshi, et al.; "Coenzyme Q10-containing emulsions, and manufacture thereof", XP002643081. English abstract of JP 2003238396.
Database GNPD (Online), (Feb. 1999), Mintel; "Verzorgende Shampoo-Lang Harr", XP002662186.
English Abstract for JPH03168075, Jul. 19, 1991.
English Abstract for JPH09291016, Nov. 11, 1997.
English Abstract for JP 2008094755, Apr. 24, 2008.
English Abstract for JP 2009078984, Apr. 16, 2009.
Christian W. Klampfl et al., "Quantitative determination of UV filters in sunscreen lotions using microemulsion electrokinetic chromatography," J. Sep. Sci. Sep. 26, 2003, 1259-1262.
Database CA (Online) Chemical Abstracts Service, Feb. 24, 1985, "Cosmetics Containing Isosrbide Fatty Acid Diesters," Database Accession No. 1985:67233. English-language abstract of JP 59-175408.
Dubini Francesco et al., "In Vitro Antimycotic Activity and Nail Permeation Models of a Prioctone Olamine (Octopirox) Containing Transungual Water Soluble Technology," Arzneimittel Forschung. Drug Research, ECV Editio Cantor Verlag, vol. 55 No. 8, pp. 478-483, Jan. 1, 2005.
English-language Abstract of JP 8173787, Jul. 9, 1996.
English-language Abstract of JP 8187070, Jul. 23, 1996.
English-language abstract of WO 2008/155159 A1, Dec. 24, 2008.
English-translation of International Preliminary Report on Patentability for PCT/EP2012/003244 dated Feb. 4, 2014.
English-translation of International Preliminary Report on Patentability for PCT/EP2012/003245 dated Feb. 21, 2014.
English-translation of International Preliminary Report on Patentability for PCT/EP2012/003246 dated Feb. 4, 2014.
English-Translation of International Preliminary Report on Patentability for PCT/EP2012/003247 dated Mar. 24, 2014.
English-Translation of International Preliminary Report on Patentability for PCT/EP2012/003248 dated Feb. 4, 2014.
English-translation of International Preliminary Report on Patentability for PCT/EP2012/003252 dated Feb. 4, 2014.
English-translation of International Preliminary Report on Patentability for PCT/EP2012/003253 dated Feb. 4, 2014.
F.C. Kull et al., Applied Microbiology 1961, 9, 538.
Frieder W. Lichtenthaler, "Carbohydrates, Chapter 9: Carbohydrates as Organic Raw Materials," Ullmann's Encyclopedia of Industrial Chemistry, vol. 6, pp. 262-273, Jan. 1, 2003.
Giacometti, J. et al., "Process for Preparing Nonionic Surfactant Sorbitan Fatty Acid Esters with and without Previous Sorbitol Cyclization", J. of Agricultural and Food Chemistry, American Chemical Society, vol. 44, Jan. 1, 1996, pp. 3950-3954.
International Search Report for PCT/EP2012/003244 dated Oct. 18, 2012.
International Search Report for PCT/EP2012/003245 dated Oct. 5, 2012.
International Search Report for PCT/EP2012/003246 dated Oct. 18, 2012.
International Search Report for PCT/EP2012/003247 dated Oct. 18, 2012.
International Search Report for PCT/EP2012/003248 dated Oct. 18, 2012.
International Search Report for PCT/EP2012/003249 dated Oct. 5, 2012.
International Search Report for PCT/EP2012/003250 dated Oct. 5, 2012.
International Search Report for PCT/EP2012/003251 dated Oct. 10, 2012.
International Search Report for PCT/EP2012/003252 dated Oct. 8, 2012.
International Search Report for PCT/EP2012/003253 dated Oct. 8, 2012.
International Search Report for PCT/EP2012/004827 dated Jan. 7, 2014.
Peter Stoss et al., "Regioselektive Acylierung von 1, 4:3, 6-Dianhydro-D-glucit," Synthesis, vol. 1987, No. 02, pp. 174-176, Jan. 1, 1987.
Seal, Kenneth J. et al., "Benzisothiazolinone and Methylisothiazolinone. New Preservative System," Cosmetic Technology, CEC, vol. 5, No. 1, pp. 47-52, Jan. 1, 2002.
Translation of International Preliminary Report on Patentability for PCT/EP2012/003249 dated Feb. 4, 2014.
Translation of International Preliminary Report on Patentability for PCT/EP2012/003250 dated Feb. 4, 2014.

(56) References Cited

OTHER PUBLICATIONS

Translation of International Preliminary Report on Patentability for PCT/EP2012/003251 dated Feb. 4, 2014.
USPTO Ex Parte Quayle Action for U.S. Appl. No. 14/237,071, dated Jun. 24, 2015.
USPTO Final Rejection for U.S. Appl. No. 13/321,178, dated Dec. 4, 2013.
USPTO Final Rejection for U.S. Appl. No. 14/237,042, dated Jul. 8, 2015.
USPTO Final Rejection for U.S. Appl. No. 14/237,053, dated Sep. 8, 2015.
USPTO Non-Final Rejection for U.S. Appl. No. 13/321,178, dated Apr. 30, 2013.
USPTO Non-Final Rejection for U.S. Appl. No. 13/321,178, dated May 6, 2014.
USPTO Non-Final Rejection for U.S. Appl. No. 14/237,024, dated Mar. 4, 2015.
USPTO Non-Final Rejection for U.S. Appl. No. 14/237,039, dated Aug. 14, 2015.
USPTO Non-Final Rejection for U.S. Appl. No. 14/237,042, dated Dec. 17, 2014.
USPTO Non-Final Rejection for U.S. Appl. No. 14/237,053, dated May 7, 2015.
USPTO Non-Final Rejection for U.S. Appl. No. 14/237,076, dated Sep. 9, 2015.
USPTO Requirement for Restriction/Election for U.S. Appl. No. 13/321,178, dated Jan. 10, 2013.
USPTO Requirement for Restriction/Election for U.S. Appl. No. 14/237,027, dated Jan. 28, 2015.
USPTO Requirement for Restriction/Election for U.S. Appl. No. 14/237,039, dated Aug. 14, 2015.
USPTO Requirement for Restriction/Election for U.S. Appl. No. 14/237,071, dated Jan. 28, 2015.
Sorbitan Caprylate—the Preservative Boosting, Multifunctional Ingredient, Frederic Pilz, Cosmetic Science Technology, 2011, pp. 131-134.
A welcome side effect: How Velsan® SC (Sorbitan Caprylate) helps to reduce the concentration of classical preservatives, Fredric Pilz, et al., Household and Personal Care Today, Mar. 2010, pp. 22-24.
Velsan SC: Caprilato de sorbitán—Ingrediente multifuncional, conservante, hidrótropo y agente co-emulsionante, Fredric Pilz, et al., NCP 322, Nov.-Dec. 2011, pp. 15-19.
A preservative-free solution, Fredric Pilz, SPC, Oct. 2011.
Presentation by Fredric Pilz, at In-Cosmetics 2010 Paris, Apr. 5, 2010.
Presentation by Fredric Pilz, at SCS Formulate, Nov. 10, 2010.
Presentation by Fredric Pilz, at HPCI Koferenz—Asien, Dec. 17, 2010.
Presentation by Fredric Pilz, at In-Cosmetics 2011 Milano, Mar. 31, 2011.
Presentation by Fredric Pilz, at HPCI Koferenz—Turkey, Jun. 2, 2011.
Translation of International Preliminary Report on Patentability for PCT/EP2012/004827 dated Jan. 7, 2014.

* cited by examiner

COMPOSITION CONTAINING SORBITAN MONOCAPRYLATE AND ALCOHOL

The present invention relates to liquid compositions containing sorbitan monocaprylate and alcohol.

The use of alcohols for preserving cosmetic, dermatological or pharmaceutical formulations and products, such as of benzyl alcohol or 1,2-octanediol, is known (David Steinberg, Preservatives for Cosmetics, Allured Publishing Corporation, second edition 2006). The maximum concentration at which the alcohols are used is mandated in part by statutory regulatory instruments—in the EU for example, by ANNEX VI of the Cosmetics Directive. It is also mandated by the viscosity-lowering effect of the alcohols in the formulation when they are used at relatively high concentrations. The lowering of the viscosity here is an unwanted side effect. Moreover, there may also be instances of phase separation within the cosmetic, dermatological or pharmaceutical formulation.

Not all antimicrobially active alcohols are dermatologically and toxicologically unobjectionable, and this is why the amount of these alcohols that is used in the cosmetic, dermatological or pharmaceutical formulation ought to be such that the formulation is just provided sufficient protection against microbial infestation. Often, however, the maximum permissible use concentration of the alcohols, or the maximum use concentration that has no adverse effect on the formulation, is not enough to provide the cosmetic, dermatological or pharmaceutical formulation with adequate protection against microbial infestation.

In order to keep the total amount of antimicrobially active alcohols in the cosmetic, dermatological or pharmaceutical formulation low, the object consisted in finding a dermatologically and toxicologically harmless substance that supports the antimicrobial action of the antimicrobially active alcohols in a synergistic manner.

Surprisingly, it has been found that the sorbitan monocaprylate already known and used in cosmetics as a surfactant and emulsifying agent fulfills exactly these conditions.

The subject of the present invention are therefore liquid compositions containing a) from 5 to 95% by weight, preferably from 10 to 90% by weight, particularly preferably from 20 to 80% by weight and especially preferably from 30 to 70% by weight, of sorbitan monocaprylate and b) from 5 to 95% by weight, preferably from 10 to 90% by weight, particularly preferably from 20 to 80% by weight and especially preferably from 30 to 70% by weight, of one or more alcohols of the formula (1)

$$R-OH \quad (1)$$

wherein R is a radical consisting of carbon, hydrogen and optionally oxygen atoms having 5-12, preferably 6-11, carbon atoms, and the carbon atoms can be linked to one another in a linear, branched and/or cyclic manner by means of saturated, unsaturated and/or aromatic carbon-carbon bonds and the radicals can also contain ether units and in which hydrogen atoms and/or hydroxyl groups can be bonded to the individual carbon atoms.

Sorbitan monocaprylate is harmless dermatologically as well as toxicologically even in very high use concentrations and supports the antimicrobial action of antimicrobially active alcohols in a synergistic manner.

It was further found that sorbitan monocaprylate does not decrease the viscosity of a cosmetic, dermatological or pharmaceutical formulation, but even, on the contrary, has slightly thickening properties. Thus, in comparison to the antimicrobially active alcohols, considerably higher amounts of sorbitan monocaprylate can be employed without lowering the viscosity of the cosmetic, dermatological or pharmaceutical formulation or favoring a phase separation.

The use concentration of antimicrobially active alcohols needed for an adequate preservation of the cosmetic, dermatological or pharmaceutical formulation can be significantly decreased in combination with sorbitan monocaprylate. By this means, the use of an antimicrobially active alcohol often suffices for the preservation of the cosmetic, dermatological or pharmaceutical formulation.

Sorbitan monocaprylate is liquid at room temperature and miscible with the antimicrobially active alcohols.

Advantageous to the liquid and therefore easily manageable compositions according to the invention is, for example, their good formulatability.

Preferably, the one or more alcohols of the formula (1) is/are selected from the group consisting of aromatic alcohols, aikanediols and alkanetriols, and particularly preferably the one or more alcohols of the formula (1) is/are selected from the group consisting of aromatic alcohols and alkanediols.

Especially preferably, the one or more alcohols of the formula (1) is/are selected from the group of alcohols consisting of benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol and ethylhexylglycerol wherein, among the aromatic alcohols, benzyl alcohol and phenoxyethanol are in turn preferred and benzyl alcohol is particularly preferred.

In one preferred embodiment of the invention, component b) of the liquid compositions according to the invention comprises one or more alcohols in the formula (1) selected from aromatic alcohols, preferably at least 50% by weight, particularly preferably 60 to 100% by weight and especially preferably 100% by weight of one or more alcohols of the formula (1) selected from aromatic alcohols, the one or more aromatic alcohols being selected preferably from benzyl alcohol, phenoxyethanol, propylene phenoxyethanol and phenethyl alcohol, and particularly preferably from benzyl alcohol and phenoxyalcohol, and the one or more aromatic alcohols especially preferably being benzyl alcohol.

Among the liquid compositions according to the invention that have just been stated, one preferred embodiment of the invention gives preference in turn to those where component b), in addition to the one or more alcohols of the formula (1) selected from aromatic alcohols, comprises one or more nonaromatic alcohols, preferably selected from the group of the alkanediols consisting of 1,2-hexanediol, 1,6-hexanediol, 1,2-octanediol, 1,2-decanediol and ethylhexylglycerol.

In another preferred embodiment of the invention, component b) of the liquid compositions according to the invention comprises one or more alcohols of the formula (1) selected from alkanediols and alkanetriols, and preferably alkanediols, preferably at least 50% by weight, particularly preferably 60 to 100% by weight and especially preferably 100% by weight of one or more alcohols of the formula (1) selected from alkanediols and alkanetriols, and preferably alkanediols, the one or more alkanediols being selected preferably from 1,2-hexanediol, 1,6-hexanediol, 1,2-octanediol, 1,2-decanediol and ethylhexylglycerol, and particularly preferably from 1,2-octanediol and ethylhexylglycerol.

In a particularly preferred embodiment of the invention, the liquid compositions according to the invention contain one or more other substances selected from d) water e) antimicrobial active ingredients and f) hydrotropes, in which the antimicrobial active ingredients and hydrotropes are different to the alcohols of the formula (1).

The antimicrobial active ingredients of component e) and the hydrotropes of component f) are different to sorbitan monocaprylate.

In a particularly preferred embodiment of the invention, the liquid compositions according to the invention contain water. In a hereunder in turn preferred embodiment of the invention, the water is contained in the liquid compositions according to the invention in an amount from 0.1 to 35% by weight, preferably from 0.1 to 20% by weight and particularly preferably from 0.5 to 10% by weight.

In a further particularly preferred embodiment of the invention, the liquid compositions according to the invention contain one or more antimicrobial active ingredients, which are different to the alcohols of the formula (1).

These antimicrobial active ingredients are preferably selected from piroctone olamine(2-aminoethanol salt of 1-hydroxy-4-methyl-6-(2,4,4-trimethylpentyl)-2(1H)-pyridone, commercial product is Octopirox®), parabens, such as, for example, methylparaben, ethylparaben, propylparaben, isopropylparaben, butylparaben, isobutylparaben, sodium methylparaben, sodium ethylparaben, sodium propylparaben, sodium isobutylparaben, sodium isopropylparaben or sodium butylparaben, organic acids and salts thereof, such as, for example, benzoic acid, sorbic acid, 3-actyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid, 2,4-hexanedienoic acid and/or salts thereof such, for example, sodium benzoate, potassium sorbate or salicylates such as, for example, sodium salicylate, imidazolidinyl urea, diazolidinyl urea, iodopropynyl butylcarbarnate, 2-bromo-2-nitropropane-1,3-diol, cetyltrimethylammonium chloride, cetylpyridinium chloride, benzethonium chloride, diisobutylethoxyethyl dimethylbenzylammonium chloride, diisobutylphenoxyethoxyethyl dimethylbenzylammonium chloride, N-alkyl-N,N-dimethylbenzylammonium chloride, bromide or saccharinate, trimethyl-ammonium chloride, sodium aluminum chlorohydroxylactate, triethyl citrate, tricetylmethylammonium chloride, 2,4,4'-trichloro-2'-hydroxydiphenyl ether(triclosan), 3,4,4'-trichiorocarbanilide(triclocarban), diaminoalkylamide, for example L-lysine hexadecylamide, DMDM hydantoin, sodium hydroxymethylglycinate, 2-hydroxybiphenyl, chlorbutanulum, 5-amino-1,3-bis(2-ethylhexyl)-5-methylhexahydropyrimidine, 2,4-dichloro-benzyl alcohol, N-(4-chlorophenyl-N'-(3,4-dichlorophenyl)urea, 2,4,4'-trichloro-2'-hydroxydiphenyl ether, poly(hexamethylenediguanide) hydrochloride, 1,2-dibromo-2,4-dicyanobutane, 4,4-dimethyl-1,3-oxazolidine, isothiazolinones, for example methylisothiazolinone or methylchloroisothiazolinone and methylisothiazolinone in a molar ratio of 3:1, chloroxylenol, citrate heavy-metal salts, silver chloride, piroctose, in particular zinc salts, pyrithiones and their heavy-metal salts, especially zinc pyrithione, zinc phenolsulfate, farnesol, bifonazole, butoconazole, cloconazole, clotrimazole, econazole, enilconazole, fenticonazole, fluconazole, isoconazole, itraconazole, ketoconazole, miconazole, naftifine, oxiconazole, suiconazole, terbinafine, terconazole and tioconazole and combinations of these active substances.

In an especially preferred embodiment of the invention, the liquid compositions according to the invention contain one or more antimicrobial active ingredients, which are different to the alcohols of the formula (1), selected from parabens, preferably methylparaben, ethylparaben, propylparaben, butylparaben, isobutylparaben, sodium methylparaben, sodium ethylparaben, sodium propylparaben, sodium isobutylparaben and/or sodium butylparaben, organic acids and salts thereof, preferably benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and/or salts thereof such as, for example, sodium benzoate, potassium sorbate and/or sodium salicylate, formaldehyde donors, preferably imidazolidinyl urea, diazolidinyl urea, DMDM hydantoin and/or sodium hydroxymethyiglycinate, halogenated preservatives, preferably iodopropynyl butyl-carbamate and/or, 2-bromo-2-nitropropane-1,3-diol, and isothiazolinones, preferably methylisothiazolinone.

In an extremely preferred embodiment of the invention, the liquid compositions according to the invention contain one or more antimicrobial active ingredients, which are different to the alcohols of the formula (1), selected from organic acids and their salts, preferably selected from benzoic acid, sorbic acid, 3-acetyl-6-methyl-2[H]-pyran-2,4 [3H]-dione (dehydroacetic acid), p-methoxybenzoic acid, formic acid, acetic acid, propionic acid, lactic acid, undecenoic acid, salicylic acid, glycolic acid and salts thereof.

If the liquid compositions according to the invention contain one or more antimicrobial active ingredients that are different to the alcohols of the formula (1), these are preferably contained in the liquid compositions according to the invention in an amount from 0.5 to 30% by weight and particularly preferably from 1.0 to 25% by weight.

In the case that the liquid compositions according to the invention contain one or more other antimicrobial active ingredients selected from salts of organic acids, the liquid compositions according to the invention preferably contain from 2 to 35% by weight, particularly preferably from 5 to 20% by weight and especially preferably from 10 to 15% by weight, of water.

In a further particularly preferred embodiment of the invention, the liquid compositions according to the invention contain one or more hydrotropes that are different to the alcohols of the formula (1). These hydrotropes are preferably selected from xylene, toluene and cumene sulfonate, Cumene sulfonate is particularly preferred.

If the liquid compositions according to the invention contain one or more hydrotropes that are different to the alcohols of the formula (1), the amount of the one or more of these hydrotropes in the liquid compositions according to the invention is preferably in the range from 1 to 15% by weight, particularly preferably from 4 to 10% by weight and especially preferably from 6 to 8% by weight.

In a further particularly preferred embodiment of the invention, the liquid compositions according to the invention contain one or more other additives.

These further additives are preferably selected from antioxidants and solubilizers.

In a further particularly preferred embodiment of the invention, the liquid compositions according to the invention contain one or more antioxidants.

The antioxidants are preferably selected from superoxide dismutase, tocopherol (vitamin E), ascorbic acid (vitamin C), amino acids (e.g. glycine, histidine, tyrosine, tryptophan) and their derivatives, imidazoles (e.g. urocaninic acid) and their derivatives, peptides such as D,L-carnosine, D-carnosine, L-carnosine and their derivatives (e.g. anserine), carotenoids, carotenes (e.g. α-carotene, β-carotene, lycopene)

and their derivatives, chlorogenic acid and its derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) as well as their salts, dilauryl thiodipropionate, distearyl thiodipropionate, thiodipropionic acid and its derivatives (esters, ethers, peptides, lipids, nucleotides, nucleosides and salts) as well as sulfoximine compounds (e.g. buthionine sulfoximine, homocysteine sulfoximine, buthionine sulfone, penta-, hexa-, heptathionine sulfoximine) in very small tolerable doses (e.g. pmol/kg), furthermore (metal) cheiators (e.g. α-hydroxy fatty acids, palmitic acid, phytic acid, lactoferrin), α-hydroxy acids (e,g, citric acid, lactic acid, malic acid), humic acid, phytic acid, gallic acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), coniferyl benzoate of benzoin resin, rutic acid and its derivatives, α-glycosylrutin, ferulic acid, furfurylidene glucitol, carnosine, butylhydroxyanisole, nordihydroguaiac resin acid, nordihydrogualaretic acid, trihydroxybutyrophenone, uric acid and its derivatives, mannose and its derivatives, zinc and its derivatives (e.g. ZnO, $ZnSO_4$) selenium and its derivatives (e.g. selenomethionine), stilbenes and their derivatives (e.g. stilbene oxide, trans-stilbene oxide) and superoxide dismutase and suitable derivatives according to the invention (salts, esters, ethers, sugars, nucleotides, nucleosides, peptides and lipids) of these said substances.

Particularly preferred antioxidants are selected from oil-soluble antioxidants.

Especially preferred antioxidants are selected from tocopheryl acetate and EDTA.

If the liquid compositions according to the invention contain one or more antioxidants, these are preferably contained in the liquid compositions according to the invention in an amount from 0.001 to 30% by weight, particularly preferably from 0.05 to 20% by weight and especially preferably from 0.1 to 5% by weight.

In a further particularly preferred embodiment of the invention, the liquid compositions according to the invention contain one or more solubilizers.

Preferred solubilizers are compounds selected from the group consisting of ethanol, propanol, isopropanol, n-butanol, isobutanol, butylene glycol, 1,2-propylene glycol, polyethylene glycols having a relative molecular mass of 300 to 2000, especially having a relative molecular mass of 300 to 600, triacetin (glycerol triacetate), 1-methoxy-2-propanol and PEG 4-laurate (polyethylene glycol 4-laurate).

Particularly preferred solubilizers are selected from butylene glycol and 1,2-propylene glycol.

If the liquid compositions according to the invention contain one or more solubilizers, these are preferably contained in the liquid compositions according to the invention in an amount from 1 to 20% by weight.

In a further particularly preferred embodiment of the invention, the liquid compositions according to the invention contain less than 5% by weight, preferably less than 3% by weight and particularly preferably less than 1% by weight, of water. In an especially preferred embodiment of the invention, the liquid compositions according to the invention contain no water, i.e. they are anhydrous.

In a further particularly preferred embodiment of the invention, the liquid compositions according to the invention consist of
 a) sorbitan monocaprylate and
 b) one or more alcohols of the formula (1).

In a further particularly preferred embodiment of the invention, the liquid compositions according to the invention consist of
 a) sorbitan monocaprylate and
 b) one or more alcohols of the formula (1) and
 d) water.

In a further particularly preferred embodiment of the invention, the liquid compositions according to the invention consist of
 a) sorbitan monocaprylate and
 b) one or more alcohols of the formula (1) and
 e) one or more antimicrobial active ingredients that are different to the alcohols of the formula (1), In a further particularly preferred embodiment of the invention, the liquid compositions according to the invention consist of
 a) sorbitan monocaprylate and
 b) one or more alcohols of the formula (1),
 d) water and
 e) one or more antimicrobial active ingredients that are different to the alcohols of the formula (1).

Preferably, the liquid compositions according to the invention have a clear appearance.

The liquid compositions according to the invention are advantageously suitable for preserving cosmetic, dermatological or pharmaceutical products.

A further subject of the invention is therefore the use of a liquid composition according to the invention for preserving cosmetic, dermatological or pharmaceutical products, preferably creams, cream gels, lotions, shampoos, shower baths, deodorants, antiperspirants, wet wipes, sunscreen formulations or decorative cosmetic articles. In a preferred embodiment of the invention, cosmetic, dermatological or pharmaceutical formulations are preserved.

The liquid compositions according to the invention are furthermore advantageously suitable for the production of cosmetic, dermatological or pharmaceutical products, preferably of cosmetic, dermatological or pharmaceutical formulations.

A further subject of the present invention is therefore the use of a liquid composition according to the invention for the production of cosmetic, dermatological or pharmaceutical products and preferably of cosmetic, dermatological or pharmaceutical formulations.

The term "cosmetic, dermatological or pharmaceutical products" is understood in the context of the present invention as meaning, for example, corresponding formulations.

The cosmetic, dermatological or pharmaceutical products can be, for example, aqueous, aqueous-alcoholic, aqueous-surfactant or alcoholic agents or compositions based on oil, including compositions based on oil in anhydrous form or emulsions, suspensions or dispersions, namely in the form of fluids, foams, sprays, gels, mousse, lotions, creams, powders or wet wipes.

In a preferred embodiment of the invention, the liquid compositions according to the invention are used for preserving wet wipes. In this case, the formulation for preserving applied to the textile fabric can be an emulsion, especially an O/W emulsion, but also a surfactant formulation or an oily composition.

In a further preferred embodiment of the invention, the liquid compositions according to the invention are used for preserving emulsions.

The emulsions can be both water-in-oil emulsions and oil-in-water emulsions, microemulsions, nanoemulsions and multiple emulsions. The production of the emulsions can be carried out in a known manner, i.e. for example by cold, hot, hot/cold or PIT emulsification. Self-foaming, foamy, after-foaming or foamable emulsions and microemulsions are a particularly preferred embodiment of the invention.

A further subject of the present invention is cosmetic, dermatological or pharmaceutical products, preferably cosmetic, dermatological or pharmaceutical formulations, that have been prepared using a liquid composition according to the invention that contains
a) sorbitan monocaprylate and
b) one or more alcohols of the formula (1)

R—OH     (1)

wherein R is a radical consisting of carbon, hydrogen and optionally oxygen atoms having 5-12, preferably 6-11, carbon atoms, and the carbon atoms can be linked to one another in a linear, branched and/or cyclic manner by means of saturated, unsaturated and/or aromatic carbon-carbon bonds and the radicals can also contain ether units and in which hydrogen atoms and/or hydroxyl groups can be bonded to the individual carbon atoms, or cosmetic, dermatological or pharmaceutical products, preferably cosmetic, dermatological or pharmaceutical formulations, that contain such a liquid composition.

A further subject of the present invention is cosmetic, dermatological or pharmaceutical products, preferably cosmetic, dermatological or pharmaceutical formulations, containing
a) sorbitan monocaprylate and
b) one or more alcohols of the formula (1)

R—OH     (1)

wherein R is a radical consisting of carbon, hydrogen and optionally oxygen atoms having 5-12, preferably 6-11, carbon atoms, and the carbon atoms can be linked to one another in a linear, branched and/or cyclic manner by means of saturated, unsaturated and/or aromatic carbon-carbon bonds and the radicals can also contain ether units and in which hydrogen atoms and/or hydroxyl groups can be bonded to the individual carbon atoms.

In a preferred embodiment of the invention, the cosmetic, dermatological or pharmaceutical products, preferably the cosmetic, dermatological or pharmaceutical formulations, contain
a) sorbitan monocaprylate,
b) one or more alcohols of the formula (1)

R—OH     (1)

wherein R is a radical consisting of carbon, hydrogen and optionally oxygen atoms having 5-12, preferably 6-11, carbon atoms, and the carbon atoms can be linked to one another in a linear, branched and/or cyclic manner by means of saturated, unsaturated and/or aromatic carbon-carbon bonds and the radicals can also contain ether units and in which hydrogen atoms and/or hydroxyl groups can be bonded to the individual carbon atoms, and
e) one or more antimicrobial active ingredients that are different to the alcohols of the formula (1).

Among the cosmetic, dermatological or pharmaceutical products according to the invention just mentioned, especially the cosmetic, dermatological or pharmaceutical formulations according to the invention, those are preferred in which the one or the more antimicrobial active ingredients of component e) are selected from parabens, preferably methylparaben, ethylparaben, propylparaben, butylparaben, isobutylparaben, sodium methylparaben, sodium ethylparaben, sodium propylparaben, sodium isobutylparaben and/or sodium butylparaben, organic acids and salts thereof, preferably benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and/or salts thereof, such as, for example, sodium benzoate, potassium sorbate and/or sodium salicylate, formaldehyde donors, preferably imidazolidinyl urea, diazolidinyl urea, hydantoin and/or sodium hydroxymethyiglycinate, halogenated preservatives, preferably iodopropynyl butyl-carbamate and/or 2-bromo-2-nitropropane-1,3-diol, and isothiazolinones, preferably methylisothiazolinone.

Particularly preferred cosmetic, dermatological or pharmaceutical products according to the invention, especially cosmetic, dermatological or pharmaceutical formulations according to the invention, are those containing
a) sorbitan monocaprylate,
b) one or more alcohols of the formula (1)

R—OH     (1)

wherein R is a radical consisting of carbon, hydrogen and optionally oxygen atoms having 5-12, preferably 6-11, carbon atoms, and the carbon atoms are linked to one another in a linear, branched and/or cyclic manner by means of saturated, unsaturated or aromatic carbon-carbon bonds or ether units and hydrogen atoms or hydroxyl groups are bonded to the carbon atoms, and
e) one or more organic acids or salts thereof, preferably selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and salts thereof.

The salts of the one or more of the organic acids mentioned under component e) are preferably
in the case of benzoic acid sodium benzoate, potassium benzoate or ammonium benzoate,
in the case of sorbic acid potassium sorbate or ammonium sorbate,
in the case of dehydroacetic acid sodium dehydroacetate, potassium dehydroacetate or ammonium dehydroacetate,
in the case of p-methoxybenzoic acid, sodium p-methoxybenzoate, potassium p-methoxybenzoate or ammonium p-methoxybenzoate,
in the case of formic acid sodium formate, potassium formate or ammonium formate,
in the case of acetic acid, sodium acetate, potassium acetate or ammonium acetate,
in the case of propionic acid sodium propionate, potassium propionate, ammonium propionate or calcium propionate,
in the case of lactic acid sodium lactate, potassium lactate, ammonium lactate or magnesium lactate,
in the case of undecenoic acid sodium undecylenate, potassium undecylenate, ammonium undecylenate, magnesium undecylenate or zinc undecylenate, in the case of salicylic acid sodium salicylate, potassium salicylate, ammonium salicylate, magnesium salicylate or zinc salicylate, and in the case of glycolic acid sodium glycolate, potassium glycolate, ammonium glycolate or magnesium glycolate.

In an especially preferred embodiment of the invention, the substances of the components a) and b), based on the finished cosmetic, dermatological or pharmaceutical products according to the invention, preferably the finished cosmetic, dermatological or pharmaceutical formulations according to the invention, are together contained to 0.1 to 4.0% by weight, preferably together to 0.3 to 3.0% by weight, particularly preferably together to 0.4 to 2.5% by weight and especially preferably together to 0.5 to 2.0% by weight in the products or formulations.

In a further especially preferred embodiment of the invention, the substances of the components a), b) and e), based on the finished cosmetic, dermatological or pharmaceutical products according to the invention, preferably the finished cosmetic, dermatological or pharmaceutical formulations according to the invention, are together contained to 0.1 to 4.0% by weight, preferably together to 0.3 to 3.0% by weight, particularly preferably together to 0.4 to 2.5% by weight and especially preferably together to 0.5 to 2.0% by weight in the products or formulations.

In a further preferred embodiment of the invention, the cosmetic, dermatological or pharmaceutical products according to the invention are rinse-off products, especially shampoos, hair rinses, hair lotions, shower baths, shower gels or foam baths.

In a further preferred embodiment of the invention, the cosmetic, dermatological or pharmaceutical products according to the invention are leave-on products, especially day creams, night creams, care creams, nutrient creams, body lotions, ointments or lip care compositions. Further preferred leave-on products are decorative cosmetics, especially make-ups, eyeshadows, lipsticks or mascara.

In a further preferred embodiment of the invention, the cosmetic, dermatological or pharmaceutical products according to the invention are sunscreens. These contain one or more UV filters on an organic or inorganic basis.

In a further preferred embodiment of the invention, the cosmetic, dermatological or pharmaceutical products according to the invention are deodorants and antiperspirants, especially in the form of sprays, sticks, gels or lotions.

In a further preferred embodiment of the invention, the cosmetic, dermatological or, pharmaceutical products according to the invention are surfactant-free compositions, especially surfactant-free solid compositions or surfactant-free emulsions.

The cosmetic, dermatological or pharmaceutical products according to the invention, preferably the cosmetic, dermatological or pharmaceutical formulations according to the invention, can contain, as further auxiliaries and additives, surfactants, emulsifiers, cationic polymers, thickeners, film formers, antimicrobial active ingredients, astringents, antioxidants, UV light-screen filters, pigments/micropigments, gelling agents, and further additives customary in cosmetics, as, for example, superfatting agents, moisturizing agents, silicones, stabilizers, conditioning agents, glycerol, preservatives, pearlizing agents, colorants, fragrance and perfume oils, solvents, hydrotropes, opacifiers, fatty alcohols, substances having keratolytic and keratoplastic action, antidandruff agents, biogenic active ingredients (local anesthetics, antibiotics, antiinflammatories, antiallergics, corticosteroids, sebostatics), vitamins, Bisabolol®, Allantoin®, Phytantriol®, Panthenol®, AHA acids (alpha-hydroxy acids), plant extracts, for example Aloe Vera, and proteins.

In a preferred embodiment of the invention, the cosmetic, dermatological or pharmaceutical products are appropriate formulations.

A further subject of the present invention is the use of sorbitan mohocaprylate for improving the antimicrobial efficacy of alcohols of the formula (1)

$$R-OH \qquad (1)$$

wherein R is a radical consisting of carbon, hydrogen and optionally oxygen atoms having 5-12, preferably 6-11, carbon atoms, and the carbon atoms can be linked to one another in a linear, branched and/or cyclic manner by means of saturated, unsaturated and/or aromatic carbon-carbon bonds and the radicals can also contain ether units and in which hydrogen atoms and/or hydroxyl groups can be bonded to the individual carbon atoms.

The production of the liquid compositions according to the invention can be carried out, for example, by adding together the individual components, optionally with slight warming to about 50° C.

The following examples and applications are intended to illustrate the invention more closely, but without restricting it thereto. All percentage details are percentages by weight (% by weight), if not explicitly stated otherwise.

EXAMPLES

I) Liquid Compositions According to the Invention

Examples 1-12

Compositions consisting of
1) 50% sorbitan monocaprylate, 50% benzyl alcohol
2) 50% sorbitan monocaprylate, 50% phenoxyethanol
3) 60% sorbitan monoceplylate, 40% 1,2-octanediol
4) 40% sorbitan monocaprylate, 30% ethylhexylglycerol, 30% 1,2-hexanediol
5) 50% sorbitan monocaprylate, 50% ethylhexylglycerol
6) 45% sorbitan monocaprylate, 30% benzyl alcohol, 20% 1,6-hexanediol, 5% water
7) 65% sorbitan monocaprylate, 25% phenoxyethanol, 10% benzoic acid
8) 70% sorbitan monocaprylate, 30% 1,2-decanediol
9) 33% sorbitan monocaprylate, 33% benzyl alcohol, 34% 1,2-octanediol
10) 50% sorbitan monocaprylate, 30% phenoxyethanol, 20% ethylhexylglycerol
11) 40% sorbitan monocaprylate, 15% 1,2 hexanediol, 20% ethylhexylglycerol, 20% dehydroacetic acid, 5% water
12) 20% sorbitan monocaprylate, 40% 1,2-octanediol, 15% phenoxyethanol, 15% potassium sorbate, 10% water The preparation of the compositions of Examples 1 to 12 was carried out by blending the individual components successively with stirring in a finger paddle agitator at stirring speeds of 200-300 revolutions/minute. In the case of the addition of organic acids, the composition was warmed to approximately 50° C. in order to obtain a homogenous mixture.

II) Synergism Between Sorbitan Monocaprylate and Alcohols of the Formula (1)

Calculation of the synergistic effect according to the formula $Q_a/Q_A + Q_b/Q_B = SE$ (synergistic effect, according to F. C. Kull et al., Applied Microbiology 1961, 9, 538), where $Q_a$=minimum inhibitory concentration of the compound A in % in the mixture used, $Q_A$=minimum inhibitory concentration of the pure substance A, $Q_b$=minimum inhibitory concentration of the compound B in % in the mixture used, and $Q_B$=minimum inhibitory concentration of the pure substance B.

Evaluation of the synergistic effect: where an SE>1 is obtained, there is an antagonistic effect; if SE=1, then the compounds are neutral in their behavior toward one another, and if SE<1, there is a synergistic effect.

Example 13

Mixtures of sorbitan monocaprylate and phenoxyethanol or benzyl alcohol, in accordance with Examples 1) and 2), were investigated. The results with respect to synergism are set out in Tables A and B. "MIC blend" here is the minimum inhibitory concentration of the respective blend.

TABLE A

Results of the investigation of a mixture of sorbitan monocaprylate and phenoxyethanol in a 50:50 weight ratio as per Example 2) (blend)

| | MIC blend | Sorbitan monocaprylate | | Phenoxyethanol | | |
|---|---|---|---|---|---|---|
| | | $Q_a$ | $Q_A$ | $Q_b$ | $Q_B$ | SE |
| Staphylococcus aureus | 0.063 | 0.0315 | 0.25 | 0.0315 | 0.125 | 0.378 |
| Aspergillus brasiliensis | 0.008 | 0.004 | 0.016 | 0.004 | 0.032 | 0.375 |

TABLE B

Results of the investigation of a mixture of sorbitan monocaprylate and benzyl alcohol in a 50:50 weight ratio as per Example 1) (blend)

| | MIC blend | Sorbitan monocaprylate | | Phenoxyethanol | | |
|---|---|---|---|---|---|---|
| | | $Q_a$ | $Q_A$ | $Q_b$ | $Q_B$ | SE |
| Staphylococcus aureus | 0.032 | 0.016 | 0.25 | 0.016 | 0.25 | 0.128 |
| Aspergillus brasiliensis | 0.008 | 0.004 | 0.016 | 0.004 | 0.063 | 0.313 |

III) Cosmetic Formulations Containing Liquid Compositions According to the Invention 12 different formulations were in each case prepared from each of the cosmetic formulations A-M listed below. In fact, each cosmetic formulation A-M was in each case prepared using the individual liquid compositions according to the invention of Examples 1 to 12.

Example A

Shampoo

| | | | |
|---|---|---|---|
| A | Genapol ® LRO paste<br>Sodium Laureth Sulfate | Clariant | 13.70% |
| | Genagen ® KB<br>Coco Betaine | Clariant | 6.00% |
| | Water | | to 100% |
| B | Sodium chloride | | 1.50% |
| C | Blend 1-12 according to the invention | Clariant | 1.50% |
| D | Citric acid (10% in water) | | 0.08% |

Preparation:

I Mix the components of A

II Add B to I with stirring

III Add C toll

IV Adjust the pH to approximately 7

Example B

Facial Cleanser

| | | | |
|---|---|---|---|
| A | Genapol ® LRO liquid<br>Sodium Laureth Sulfate | Clariant | 11.10% |
| | Perfume | | q.s. |
| B | Water | | to 100% |
| | Genagen ® 3SB<br>Coco Betaine, Sodium Cocoyl Isethionate, Sodium Methyl Cocoyl Taurate | Clariant | 23.30% |
| | Dyestuff solution | | q.s. |
| C | Blend 1-12 according to the invention | Clariant | 1.20% |
| D | Citric acid | | q.s. |

Preparation:

I Mix the components A

II Add the components of B successively to I

III Add C to II with stirring

IV If desired, adjust the pH with C

Example C

Aftershave Gel

| | | | |
|---|---|---|---|
| A | Emulsogen ® HCU<br>Undeceth-8 (and) PEG-40 Hydrogenated Castor Oil | Clariant | 1.50% |
| B | Tocopherol acetate | | 0.20% |
| | Menthol | | 0.20% |
| C | Ethanol | | 30.00% |
| D | Water | | to 100% |
| | Allantoin<br>Allantoin | Clariant | 0.20% |
| | Polyglycol 400<br>PEG-8 | Clariant | 3.00% |
| | Polyglycol 35000<br>PEG-800 | Clariant | 1.00% |
| | Blend 1-12 according to the invention | Clariant | 2.00% |
| E | Aristoflex ® AVC<br>Ammonium Acryloyldimethyltaurate/VP Copolymer | Clariant | 1.00% |

Preparation:

I Mix A and B and stir for approximately 5 minutes

II Add C to I and stir until the solution is clear

III Add the components of D successively to II

IV Add E to I and stir until a homogenous formulation is obtained

Example D

Anti-Ageing Face Cream

| A | Genapol ® T 250 | Clariant | 1.50% |
|---|---|---|---|
|   | Cetereth-25 |   |   |
|   | Genapol ® DAT | Clariant | 2.00% |
|   | PEG-150 polyglyceryl-2 Tristearate and |   |   |
|   | PEG-6 Caprylic/Capric Glyceride |   |   |
| B | Water |   | to 100% |
| C | Aristoflex ® AVC | Clariant | 2.00% |
|   | Ammonium Acryloyldimethyltaurate/VP |   |   |
|   | Copolymer |   |   |
| D | Glycolic acid 30%* |   | 6.00% |
|   | Blend 1-12 according to the invention | Clariant | 1.80% |

*adjusted to pH 4 with NaOH (content based on free glycolic acid)

Preparation:
I Dissolve A in B with stirring and gentle warming
II Add C to I and stir until the resulting gel is free from lumps
III Add the components of D to II and stir until the formulation is homogeneous

Example E

Emulsion for Baby Wet Wipes

| A | Propylene glycol |   | 3.00% |
|---|---|---|---|
|   | Blend 1-12 according to the invention | Clariant | 2.00% |
|   | Emulsogen ® HCO 040 | Clariant | 1.00% |
|   | PEG-40 Hydrogenated Castor Oil |   |   |
|   | Perfume |   | 0.20% |
| B | Hostaphat ® KL 340 D | Clariant | 1.50% |
|   | Trilaureth-4 Phosphate |   |   |
|   | Velsan ® CCT | Clariant | 0.80% |
|   | Caprylic/Capric Triglyceride |   |   |
| C | Water |   | to 100% |
|   | Tetrasodium EDTA |   | 0.10% |
| D | Aristoflex ® BLV | Clariant | 0.20% |
|   | Ammonium Acryloyldimethyltaurate/ |   |   |
|   | Beheneth-25 Methacrylate Crosspolymer |   |   |
| E | Citric acid |   | q.s. |

Preparation:
I Dissolve the components of A
II Add the components of B successively with stirring to I
III Mix the components of C
IV Add D to II
V Add III to IV with stirring
VI Adjust the pH with E to approximately pH 6

Example F

O/W Body Lotion

| A | Velsan ® CCT | Clariant | 3.50% |
|---|---|---|---|
|   | Caprylic/Capric Triglyceride |   |   |
|   | Myristyl myristate |   | 2.50% |
|   | Cetearyl alcohol |   | 2.00% |
|   | Glyceryl stearate citrate |   | 1.00% |
|   | Octyldodecanol |   | 1.00% |

-continued

| B | Aristoflex ® AVC | Clariant | 0.60% |
|---|---|---|---|
|   | Ammonium Acryloyldimethyltaurate/ |   |   |
|   | VP Copolymer |   |   |
| C | Water |   | to 100% |
|   | Glycerol |   | 7.50% |
| D | Ethanol |   | 3.00% |
|   | Dimethicone |   | 3.00% |
|   | Tocopheryl acetate |   | 1.00% |
|   | Aloe barbadensis |   | 1.00% |
|   | Blend 1-12 according to the invention | Clariant | 2.00% |
| E | Sodium hydroxide |   | q.s. |

Preparation:
I Melt the components of A at approximately 70° C.
III Mix the components of C and heat the mixture to approximately 70° C.
III Add B to I when I is completely molten
IV Add II to III
V Add the components of D to IV at 35° C.
VI Adjust the pH with E to approximately pH 6.0-6.5

Example G

Antiperspirant

| A | Locron ® L | Clariant | 30.00% |
|---|---|---|---|
|   | Aluminum Chlorohydrate |   |   |
|   | Water |   | to 100% |
|   | Polyglycol 400 | Clariant | 3.00% |
|   | PEG-8 |   |   |
|   | Ethanol |   | 17.00% |
|   | Dyestuff solution |   | q.s. |
|   | Blend 1-12 according to the invention | Clariant | 1.00% |
|   | Fragrance |   | 0.30% |
| B | Tylose ® H 4000 G4 |   | 2.50% |
|   | Hydroxyethylcellulose |   |   |

Preparation:
I Mix the components of A
II Add B to I with constant stirring. Stir further until the viscosity has reached its endpoint and the formulation is homogeneous.

Example H

Cream Rinse

| A | Genamin ® DSAP | Clariant | 2.50% |
|---|---|---|---|
|   | Distearyldimonium Chloride |   |   |
|   | Genamin ® CTAC | Clariant | 3.00% |
|   | Cetrimonium Chloride |   |   |
|   | Hostacerin ® T-3 | Clariant | 1.50% |
|   | Ceteareth-3 |   |   |
|   | Cetyl alcohol |   | 3.00% |
| B | Water |   | to 100% |
|   | Blend 1-12 according to the invention | Clariant | 1.00% |
| C | Fragrance |   | 0.30% |
|   | Dyestuff solution |   | q.s. |

Preparation:
I Melt A at approximately 75° C.
II Heat B to approximately 75"C
III Add II to I with stirring and stir until cooling to 30° C.
IV At approximately 30° C. add C to II with stirring

Example I

Hairstyling Gel

| | | | |
|---|---|---|---|
| A | Sorbitol | | 5.00% |
| | Genamin ® PQ 43 | Clariant | 0.30% |
| | Polyquaternium-43 | | |
| B | Water | | to 100% |
| C | Aristoflex ® HMB | Clariant | 2.00% |
| | Ammonium Acryloyldimethyltaurate/ | | |
| | Beheneth-25 Methacrylate Crosspolymer | | |
| D | Aminomethyl propanol | | 0.30% |
| | Aristoflex ® A 60 | Clariant | 5.00% |
| | VA/Crotonates Copolymer | | |
| | Emulsogen ® HCO 040 | Clariant | 4.00% |
| | PEG-40 Hydrogenated Castor Oil | | |
| E | Fragrance | | 0.20% |
| | Blend 1-12 according to the invention | Clariant | 1.00% |
| | Dyestuff solution | | q.s. |
| | Timiron diamond cluster MP-149 | | q.s. |
| | Mica (and) Titanium Dioxide (for EU: CI 77891) | | |

Preparation:
I Mix the components of A
II Add B to I
III Swell C in II with stirring
IV Add the components of D one after the other
V Add the components of E one after the other to IV

Example J

Make-Up Remover

| | | | |
|---|---|---|---|
| A | Velsan ® P8-3 | Clariant | 5.00% |
| | Isopropyl C12-15 Pareth-9 Carboxylate | | |
| B | Hostapon ® KCG | Clariant | 2.30% |
| | Sodium Cocoyl Glutamate | | |
| | Genagen ® CAB | Clariant | 3.00% |
| | Cocamidopropyl Betaine | | |
| | Genapol ® LA 070 | Clariant | 2.00% |
| | Laureth-7 | | |
| | Water | | to 100% |
| | Allantoin | Clariant | 0.30% |
| | Allantoin | | |
| | Aristoflex ® PEA | Clariant | 1.00% |
| | Polypropylene Terephthalate | | |
| | 1,6-Hexanediol | | 2.00% |
| | 1,2-Propanediol | | 2.00% |
| | Polyglycol 400 | Clariant | 2.00% |
| | PEG-8 | | |
| | Panthenol | | 0.50% |
| | Lutrol F 127 | | 3.00% |
| | Poloxamer 407 | | |
| | Blend 1-12 according to the invention | Clariant | 1.70% |

Preparation:
I Stir the components of B successively into A and stir until a clear solution is obtained

Example K

Lipgloss

| | | | |
|---|---|---|---|
| A | Versagel ® ME 1600 | | to 100% |
| | Hydrogenated polyisobutene (and) | | |
| | Ethylene/Propylene/Styrene Copolymer | | |
| | (and) Butylene/Ethylene/Styrene | | |
| | Copolymer | | |
| | SilCare ® silicone 31M50 | Clariant | 7.00% |
| | Caprylyl Trimethicone | | |
| | SilCare ® silicone 41M65 | Clariant | 3.00% |
| | Stearyl Dimethicone | | |
| | Jojoba oil | | 2.60% |
| | Velsan CCT | Clariant | 1.00% |
| | Capric/Caprylic Triglycerides | | |
| | Isopropyl myristate | | 7.40% |
| B | Gemtone ® Tan Opal | | 1.00 to 5.00% |
| | Mica and Iron Oxide and TiO₂ | | |
| | Lake-color | | q.s. |
| C | Blend 1-12 according to the invention | Clariant | 0.50% |
| D | Perfume | | q.s. |

Preparation:

I Heat the components of A to approximately 80-85° C. and stir until a homogenous mixture is obtained. Allow this mixture to cool to 70-75° C.

II Add B and C successively to I with stirring and stir until all constituents are dissolved III Allow to cool to 45° C. and add D to II, then fill the formulation into the casting molds

Example L

Shimmering Bronze Gel

| | | | |
|---|---|---|---|
| A | Water | | to 100% |
| B | Glycerol | | 5.00% |
| | Polyglycol 35000 S | Clariant | 0.50% |
| | PEG-800 | | |
| | Allantoin | Clariant | 0.20% |
| | Allantoin | | |
| C | Aristoflex ® AVC | Clariant | 0.60% |
| | Ammonium Acryloyldimethyltaurate/ | | |
| | VP Copolymer | | |
| | Biron MTU | | 3.00% |
| | Bismuth Oxychloride | | |
| | Flamenco ultra silk | | 4.00% |
| | Titanium Oxide (and) Mica | | |
| | Flamenco sparcle gold | | 7.00% |
| | Mica (and) Iron Oxide (and) | | |
| | Titanium Oxide | | |
| | Cloisonne satin bronze | | 5.00% |
| | Iron Oxide (and) Mica | | |
| | Gemtone Sunstone | | 2.00% |
| | Mica (and) Iron Oxide (and) | | |
| | Titanium Oxide | | |
| | Desert reflections canyon sunset | | 2.00% |
| | Mica (and) Iron Oxide (and) | | |
| | Titanium Oxide (and) Tin Oxide | | |
| | SilCare ® silicone WSI | Clariant | 1.00% |
| | proposed INCI: Glyceryl Carboxy | | |
| | Amodimethicone | | |
| D | Fragrance | | q.s. |
| | Blend 1-12 according to the invention | Clariant | 1.80% |

Preparation:

I Mix the components of B and dissolve them in A with stirring

II Mix the components of C and add them to with gentle stirring

III Stir at relatively high speed of rotation (approximately 200-250 revolutions/minute) for approximately two hours or until a homogeneous gel is obtained IV Add D to III with stirring

Example M

Suncream

| | | | |
|---|---|---|---|
| A | SilCare ® silicone WSI proposed INCI: Glyceryl Carboxy Amodimethicone | Clariant | 2.00% |
| | SilCare ® silicone 41M65 Stearyl Dimethicone | Clariant | 1.00% |
| | Dow Corning ® 246 Cyclopentasiloxane/Cyclohexasiloxane | | 11.00% |
| | Titanium dioxide UV Titan M 262 Titanium Dioxide/Dimethicone | | 10.00% |
| | Solaveil CT-100 C12-15 Alkyl Benzoate/Titanium Dioxide/Aluminum Stearate/ Polyhydroxystearic Acid/Alumina | | 10.00% |
| | Z-Cote HP1 Zinc Oxide | | 8.00% |
| | Butylene glycol | | 3.00% |
| | Hostacerin ® DGI Polyglyceryl-2 Sesquiisostearate | Clariant | 3.00% |
| | Tegosoft ® TN C12-15 Alkyl Benzoate | | 2.00% |
| | Cetiol ® 868 Ethylhexylstearate | | 2.00% |
| B | Water | | to 100% |
| | Glycerol | | 5.00% |
| | Ginko biloba extract | | 0.70% |
| | Polyglycose | | 0.20% |
| | Disodium EDTA | | 0.20% |
| | Citric acid | | 0.10% |
| | Glycerol | | 5.00% |
| | Ginko biloba extract | | 0.70% |
| C | Tocopheryl acetate | | 1.00% |
| | Blend 1-12 according to the invention | Clariant | 1.80% |
| | Sodium chloride | | 1.00% |
| | Aluminum hydroxide | | 0.30% |

Preparation:
I Melt A at approximately 80° C.
II Warm B to approximately 80° C.
III Add II to I at a stirring speed of approximately 300 revolutions/minute. Increase the stirring speed gradually to 500 revolutions/minute and keep up this speed until the end of the formulation operation. Leave the mixture to cool to 35° C.
IV Add C to HI at 35° C. with stirring and leave to cool to room temperature The compositions according to the invention of Examples 1-12 contribute to an increase in biostability in the cosmetic formulations A-M.

The invention claimed is:

1. A liquid composition consisting of
sorbitan monocaprylate,
phenoxyethanol,
water,
a surfactant,
and an antimicrobial active ingredient selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and salts thereof.

2. A liquid composition consisting of
sorbitan monocaprylate and
phenoxyethanol.

3. A liquid composition consisting of
sorbitan monocaprylate,
phenoxyethanol, and
water.

4. A liquid composition consisting of
sorbitan monocaprylate,
phenoxyethanol,
and
an antimicrobial active ingredient selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and salts thereof.

5. The liquid composition as claimed in claim 1, wherein the liquid composition has a clear appearance.

6. The liquid composition as claimed in claim 2, wherein the liquid composition has a clear appearance.

7. The liquid composition as claimed in claim 3, wherein the liquid composition has a clear appearance.

8. The liquid composition as claimed in claim 4, wherein the liquid composition has a clear appearance.

* * * * *